(12) United States Patent
Kim et al.

(10) Patent No.: US 10,213,611 B2
(45) Date of Patent: Feb. 26, 2019

(54) METHOD OF MANUFACTURING FEEDTHROUGH

(71) Applicant: OSONG MEDICAL INNOVATION FOUNDATION, Cheongju-si (KR)

(72) Inventors: Jin-Won Kim, Seoul (KR); Jin-Hee Moon, Sejong (KR); In-Ho Song, Seoul (KR); Sung-Keun Yoo, Cheongju-si (KR); Seung-A Lee, Seoul (KR); Ha-Chul Jung, Cheongju-si (KR); Dong-Jun Moon, Cheongju-si (KR); Jin-Woo Ahn, Cheongju-si (KR); Sang-Hun Lee, Cheongju-si (KR)

(73) Assignee: Osong medical innovation foundation, Cheongju-si (KR)

( * ) Notice: Subject to any disclaimer, the term of this patent is extended or adjusted under 35 U.S.C. 154(b) by 0 days.

(21) Appl. No.: 15/739,982

(22) PCT Filed: Jun. 29, 2016

(86) PCT No.: PCT/KR2016/006931
§ 371 (c)(1),
(2) Date: Dec. 26, 2017

(87) PCT Pub. No.: WO2017/003164
PCT Pub. Date: Jan. 5, 2017

(65) Prior Publication Data
US 2018/0185654 A1    Jul. 5, 2018

(30) Foreign Application Priority Data
Jun. 30, 2015  (KR) ........................ 10-2015-0092754

(51) Int. Cl.
*B23K 20/00*    (2006.01)
*A61N 1/375*    (2006.01)
(Continued)

(52) U.S. Cl.
CPC ........... *A61N 1/3754* (2013.01); *A61N 1/375* (2013.01); *B23K 20/02* (2013.01); *B23K 26/38* (2013.01); *H01G 4/35* (2013.01); *H01R 2201/12* (2013.01)

(58) Field of Classification Search
CPC ........ A61N 1/3754; A61N 1/375; H01G 4/35; H01R 2201/12; B23K 20/02;
(Continued)

(56) References Cited

U.S. PATENT DOCUMENTS 4,816,621 A * 3/1989 Huebner .............. A61N 1/3754
                                           174/152 GM
5,738,270 A * 4/1998 Malmgren ............ A61F 2/0095
                                           228/124.6
(Continued)

FOREIGN PATENT DOCUMENTS

EP    1688160 A2    8/2006
GB    2040685 A *   9/1980    ........... A61N 1/0565
(Continued)

OTHER PUBLICATIONS

International Search Report of PCT/KR2016/006931 dated Oct. 4, 2016.

*Primary Examiner* — Kiley S Stoner
(74) *Attorney, Agent, or Firm* — LEEPI (57) ABSTRACT

A method of manufacturing a feedthrough having an enhanced hermetic sealing and used for a human implantable medical device such as a deep brain stimulator, a implantable AED, a implantable spinal cord stimulator and so on. Thus, more enhanced reproducibility and productivity in the diffusion welding and the laser hole machining may be guaranteed in the present method of manufacturing the feedthrough, compared to the conventional method using the ceramic metallizing and the brazing.

5 Claims, 4 Drawing Sheets

(51) Int. Cl.
  *B23K 20/02* (2006.01)
  *B23K 26/38* (2014.01)
  *H01G 4/35* (2006.01)

(58) Field of Classification Search
  CPC .... B23K 20/001; B23K 20/04; B23K 20/026; B23K 26/38–26/389
  USPC ................ 228/193–195; 219/121.65–121.72
  See application file for complete search history.

(56) References Cited

U.S. PATENT DOCUMENTS

| | | | | |
|---|---|---|---|---|
| 5,817,984 A * | 10/1998 | Taylor | H01B 17/305 | 174/152 GM |
| 5,867,361 A * | 2/1999 | Wolf | H01G 9/10 | 361/302 |
| 6,008,980 A * | 12/1999 | Stevenson | H01G 4/35 | 361/302 |
| 6,159,560 A * | 12/2000 | Stevenson | C23C 14/021 | 427/118 |
| 6,349,025 B1 * | 2/2002 | Fraley | A61N 1/3754 | 361/302 |
| 6,414,835 B1 * | 7/2002 | Wolf | A61N 1/3754 | 361/302 |
| 6,415,182 B1 * | 7/2002 | Ibrahim | A61N 1/3754 | 174/50.52 |
| 6,516,228 B1 * | 2/2003 | Berrang | H04R 25/606 | 607/57 |
| 6,529,103 B1 * | 3/2003 | Brendel | A61N 1/3754 | 333/182 |
| 7,035,076 B1 * | 4/2006 | Stevenson | H01G 4/35 | 361/302 |
| 7,736,191 B1 * | 6/2010 | Sochor | A61N 1/3752 | 439/668 |
| 7,747,321 B2 * | 6/2010 | Fischbach | A61N 1/3754 | 607/36 |
| 7,794,256 B1 * | 9/2010 | Sochor | H01R 13/025 | 439/289 |
| 7,837,085 B1 * | 11/2010 | Tziviskos | A61N 1/3754 | 228/122.1 |
| 8,000,804 B1 * | 8/2011 | Wessendorf | A61N 1/36046 | 607/115 |
| 8,162,684 B1 * | 4/2012 | Sochor | A61N 1/3754 | 439/289 |
| 8,267,708 B1 * | 9/2012 | Sochor | A61N 1/3754 | 439/289 |
| 8,501,547 B2 | 8/2013 | Greenberg et al. | | |
| 8,642,887 B1 * | 2/2014 | Li | A61N 1/3754 | 174/50.6 |
| 8,698,006 B2 | 8/2014 | Bealka et al. | | |
| 8,991,680 B1 * | 3/2015 | Schulman | A61N 1/0531 | 228/180.1 |
| 2001/0048580 A1 * | 12/2001 | Tanida | H01G 4/228 | 361/303 |
| 2002/0128692 A1 * | 9/2002 | Imani | A61N 1/3752 | 607/37 |
| 2003/0050549 A1 * | 3/2003 | Sochor | A61N 1/0529 | 600/378 |
| 2003/0179536 A1 * | 9/2003 | Stevenson | A61N 1/3754 | 361/302 |
| 2003/0195602 A1 * | 10/2003 | Boling | A61N 1/05 | 607/122 |
| 2005/0007718 A1 * | 1/2005 | Stevenson | A61N 1/3754 | 361/118 |
| 2006/0173259 A1 * | 8/2006 | Flaherty | A61B 5/0031 | 600/331 |
| 2006/0175071 A1 * | 8/2006 | Knappen | A61N 1/3754 | 174/50.56 |
| 2006/0247539 A1 * | 11/2006 | Schugt | A61B 5/0215 | 600/486 |
| 2006/0247714 A1 * | 11/2006 | Taylor | A61N 1/3754 | 607/36 |
| 2006/0259093 A1 * | 11/2006 | Stevenson | A61N 1/3754 | 607/37 |
| 2007/0019362 A1 * | 1/2007 | Stevenson | A61N 1/3752 | 361/302 |
| 2007/0067007 A1 * | 3/2007 | Schulman | A61N 1/0526 | 607/115 |
| 2007/0134985 A1 * | 6/2007 | Frysz | H01G 4/232 | 439/620.09 |
| 2007/0142888 A1 * | 6/2007 | Chavez | A61N 1/05 | 607/116 |
| 2007/0183118 A1 * | 8/2007 | Fu | A61N 1/3754 | 361/302 |
| 2007/0239222 A1 * | 10/2007 | Sprain | A61N 1/3754 | 607/37 |
| 2007/0250142 A1 * | 10/2007 | Francis | A61L 31/082 | 607/116 |
| 2007/0277374 A1 * | 12/2007 | Suaning | A61N 1/3754 | 29/831 |
| 2008/0060844 A1 * | 3/2008 | Teske | A61N 1/372 | 174/667 |
| 2008/0269596 A1 * | 10/2008 | Revie | G06F 19/00 | 600/424 |
| 2009/0240099 A1 * | 9/2009 | Conn | A61N 1/0541 | 600/25 |
| 2010/0109958 A1 * | 5/2010 | Haubrich | A61N 1/37229 | 343/718 |
| 2010/0109966 A1 * | 5/2010 | Mateychuk | A61N 1/37229 | 343/841 |
| 2010/0114246 A1 * | 5/2010 | Yamamoto | A61N 1/37223 | 607/60 |
| 2010/0168817 A1 * | 7/2010 | Yamamoto | A61N 1/37229 | 607/60 |
| 2010/0241195 A1 * | 9/2010 | Meadows | A61N 1/0556 | 607/62 |
| 2010/0241206 A1 * | 9/2010 | Truex et al. | A61B 5/0031 | 607/116 |
| 2010/0274313 A1 * | 10/2010 | Boling | A61N 1/0546 | 607/46 |
| 2010/0292760 A1 * | 11/2010 | Leigh | A61N 1/08 | 607/57 |
| 2011/0000699 A1 * | 1/2011 | Bealka | H01G 4/35 | 174/151 |
| 2011/0004076 A1 * | 1/2011 | Janna | A61B 5/0031 | 600/302 |
| 2011/0048770 A1 * | 3/2011 | Reiterer | A61N 1/3754 | 174/152 GM |
| 2011/0147062 A1 * | 6/2011 | Stevenson | H01G 4/35 | 174/260 |
| 2011/0230937 A1 * | 9/2011 | Boutaud | A61N 1/3754 | 607/62 |
| 2011/0232961 A1 * | 9/2011 | Teske | A61N 1/3754 | 174/650 |
| 2011/0232962 A1 * | 9/2011 | Teske | A61N 1/3754 | 174/650 |
| 2011/0235239 A1 * | 9/2011 | Teske | A61N 1/3754 | 361/500 |
| 2011/0284284 A1 * | 11/2011 | Talamine | A61N 1/3754 | 174/650 |
| 2011/0297439 A1 * | 12/2011 | Talamine | A61N 1/3754 | 174/650 |
| 2011/0303458 A1 * | 12/2011 | Sutay | H01G 4/232 | 174/650 |
| 2012/0165902 A1 * | 6/2012 | Sommer | A61N 1/056 | 607/60 |
| 2012/0221074 A1 * | 8/2012 | Funderburk | A61N 1/3752 | 607/45 |
| 2012/0307416 A1 * | 12/2012 | Iyer | A61N 1/3754 | 361/302 |
| 2013/0207863 A1 * | 8/2013 | Joshi | A61N 1/37229 | 343/789 |
| 2013/0286536 A1 * | 10/2013 | Iyer | A61N 1/3754 | 361/302 |
| 2013/0319717 A1 * | 12/2013 | Koester | A61N 1/3754 | 174/50.5 |
| 2013/0331923 A1 * | 12/2013 | Koester | A61N 1/3754 | 607/137 |

(56) References Cited

U.S. PATENT DOCUMENTS

| | | | |
|---|---|---|---|
| 2014/0020951 A1* | 1/2014 | Shah | A61N 1/3754 174/667 |
| 2014/0144694 A1* | 5/2014 | Shah | A61N 1/3754 174/650 |
| 2014/0163579 A1* | 6/2014 | Tischendorf | A61N 1/36139 606/129 |
| 2014/0214133 A1* | 7/2014 | Thenuwara | A61N 1/3754 607/62 |
| 2014/0235930 A1* | 8/2014 | Callaway | A61M 1/127 600/16 |
| 2014/0254124 A1* | 9/2014 | Raje | H05K 13/0465 361/808 |
| 2014/0266921 A1* | 9/2014 | Joshi | H01Q 1/24 343/702 |
| 2014/0272457 A1* | 9/2014 | Watada | B32B 15/04 428/633 |
| 2014/0277260 A1* | 9/2014 | Khalil | A61N 1/37241 607/46 |
| 2014/0371835 A1* | 12/2014 | Powell | B23K 1/0008 607/137 |
| 2015/0045861 A1* | 2/2015 | Goldman | A61N 1/3754 607/116 |
| 2015/0045862 A1* | 2/2015 | Goldman | G01R 31/1227 607/116 |
| 2015/0051676 A1* | 2/2015 | Van Funderburk | A61N 1/3754 607/116 |
| 2015/0088226 A1* | 3/2015 | Tourrel | A61N 1/3752 607/57 |
| 2015/0174415 A1* | 6/2015 | Angara | A61N 1/3787 607/46 |
| 2015/0174416 A1* | 6/2015 | Angara | H02J 7/025 607/46 |
| 2015/0180271 A1* | 6/2015 | Angara | A61N 1/3787 607/46 |
| 2015/0202706 A1* | 7/2015 | Brosnan | B23K 37/0426 439/78 |
| 2015/0238768 A1* | 8/2015 | Bornzin | A61N 1/37205 607/28 |
| 2015/0250386 A1* | 9/2015 | Jose James | A61N 1/375 600/407 |
| 2015/0265171 A1* | 9/2015 | Seaver | A61B 5/031 600/561 |
| 2015/0273219 A1* | 10/2015 | Perraud | A61N 1/3754 228/124.6 |
| 2016/0015976 A1* | 1/2016 | Biele | A61N 1/36071 607/46 |
| 2016/0015977 A1* | 1/2016 | Biele | A61N 1/36071 607/46 |
| 2016/0015980 A1* | 1/2016 | Biele | A61N 1/36178 607/46 |
| 2016/0015981 A1* | 1/2016 | Biele | A61N 1/36185 607/46 |
| 2016/0015982 A1* | 1/2016 | Biele | A61N 1/36185 607/46 |
| 2016/0045724 A1* | 2/2016 | Lee | A61N 1/0558 604/20 |
| 2016/0045746 A1* | 2/2016 | Jiang | A61N 1/37241 607/40 |
| 2016/0045747 A1* | 2/2016 | Jiang | A61N 1/37241 607/40 |
| 2016/0045751 A1* | 2/2016 | Jiang | A61N 1/37264 607/59 |
| 2016/0104947 A1* | 4/2016 | Roos | H01R 4/02 174/667 |
| 2016/0181730 A1* | 6/2016 | Eldridge | A61M 1/12 600/16 |
| 2016/0199657 A1* | 7/2016 | Jiang | A61N 1/3787 607/61 |
| 2016/0199658 A1* | 7/2016 | Nassif | A61N 1/36125 607/46 |
| 2016/0199659 A1* | 7/2016 | Jiang | A61N 1/36128 607/60 |
| 2016/0233656 A1* | 8/2016 | Thom | H02G 3/22 |
| 2016/0271400 A1* | 9/2016 | Kronmueller | A61N 1/3754 |
| 2016/0271401 A1* | 9/2016 | Klenner | A61N 1/3754 |
| 2016/0276769 A1* | 9/2016 | Pscherer | A61N 1/3754 |
| 2017/0007836 A1* | 1/2017 | Nassif | A61N 1/36125 |
| 2017/0030791 A1* | 2/2017 | Buck | G01L 9/008 |
| 2017/0036026 A1* | 2/2017 | Curtis | A61N 1/36071 |
| 2017/0072199 A1* | 3/2017 | Biele | A61N 1/36125 |
| 2017/0113032 A1* | 4/2017 | Sontheimer | A61N 1/02 |
| 2017/0113046 A1* | 4/2017 | Fried | A61B 5/6868 |
| 2017/0151438 A1* | 6/2017 | Orinski | A61N 1/3606 |
| 2017/0202092 A1* | 7/2017 | Li | H05K 3/328 |
| 2017/0216609 A1* | 8/2017 | Nassif | A61N 1/3605 |
| 2017/0222195 A1* | 8/2017 | Hartl | H01G 2/103 |
| 2017/0225007 A1* | 8/2017 | Orinski | A61N 5/0622 |
| 2017/0281944 A1* | 10/2017 | Khalil | A61N 1/3787 |
| 2017/0291029 A1* | 10/2017 | Khalil | A61N 1/36071 |
| 2017/0309499 A1* | 10/2017 | Oi | H01L 21/4882 |
| 2018/0236234 A1* | 8/2018 | Santogrossi | A61N 1/36038 |
| 2018/0236244 A1* | 8/2018 | Stevenson | A61N 1/3754 |

FOREIGN PATENT DOCUMENTS

| | | |
|---|---|---|
| JP | 2015-016297 A | 1/2015 |
| KR | 10-2014-0025466 A | 12/2012 |
| KR | 10-2013-0084626 A | 7/2013 |

\* cited by examiner

METHOD OF MANUFACTURING FEEDTHROUGH

BACKGROUND

1. Field of Disclosure

The present disclosure of invention relates to a method of manufacturing a feedthrough, and more specifically the present disclosure of invention relates to a method of manufacturing a feedthrough having an enhanced hermetic sealing and used for a human implantable medical device such as a deep brain stimulator, a implantable AED, a implantable spinal cord stimulator and so on.

2. Description of Related Technology

Recently, various kinds of human implantable medical device such as, pacemaker, implantable, cardioverter defibrillator (ICD), deep brain stimulator (DBS), spinal stimulation system, and so on, are in the market.

Such devices are manufactured using a titanium to increase biological adaptation. Here, a feedthrough is necessary to electrically connect an electric stimulating circuit inside of the titanium package of the devices to outer stimulating electrodes. Generally, a titanium flange, a ceramic structure and a platinum/iridium pin are welded to manufacture the feedthrough, and in manufacturing the feedthrough, brazing, metallizing, hermetic sealing, etc. are used.

The titanium is a reactive metal and is easy to be oxidized, and such oxidization rapidly decreases a strength of the brazing, and thus a reliability in the brazing is decreased and the brazing is more complicated. For example, in the brazing, a titanium oxidization layer is removed, a flux is coated and a gas in a chamber is accurately controlled, to block the oxidization of titanium. In addition, a surface of a ceramic is metallized using a paste having MoMn as a main material, and nickel (Ni) is coated on the metallized ceramic.

In such multi-step brazing, all steps should be performed using harmless materials, and thus a material of a filler metal used for welding the titanium with the ceramic is limited. In addition, an bad effect of a small amount of impurity added to the paste having MoMn on a human body is considered.

Further, in metallizing a surface of the ceramic structure for welding the ceramic structure with the platinum/iridium pin, a size of a hole of the ceramic structure into which the platinum/iridium pin is inserted is very small such that the metalizing is hard to be performed.

The conventional method for manufacturing the feedthrough using the ceramic metallizing and the brazing, has the following problems.

First, titanium which is a reactive metal, is easily oxidized in the brazing, and thus reproducibility of the feedthrough having hermetic sealing is decreased.

Second, the steps are very complicated, for example, removing the titanium oxidization layer to enhance the hermetic sealing, coating the flux, controlling the gas in the chamber very accurately, and so on.

Third, the paste having MoMn as the main material is used in metallizing and the nickel is coated on the metallized ceramic, but a diameter of the hole of the ceramic into which the platinum/iridium pin is inserted is too small so that the metallizing and the coating are not easy to be performed.

Fourth, the human implantable medical device has biological adaptation, and thus the flux used for preventing the oxidization of titanium in the brazing, and the filler metal used for welding the titanium with the ceramic are limited.

Fifth, in a method for manufacturing the feedthrough having the hermetic sealing via diffusion welding using a feedthrough pin having a nail head, the nail head is hard to be manufactured via forging or casting.

Related prior arts are Korean laid-open patent application No. 10-2013-7030389 and Korean laid-open patent application No. 10-2013-0004752.

SUMMARY

The present invention is developed to solve the above-mentioned problems of the related arts. The present invention provides a method of manufacturing a feedthrough having an enhanced hermetic sealing and used for a human implantable medical device such as a deep brain stimulator, a implantable AED, a implantable spinal cord stimulator and so on.

In addition, the present invention provides a method of manufacturing a feedthrough capable of forming a feedthrough body using a dual diffusion welding, forming a pin hole in the body using a laser machining, and forming a pin in the body using a capillary phenomenon.

In addition, the present invention provides a method of manufacturing a feedthrough capable of excluding removing the oxidization layer, excluding using the flux to prevent the titanium oxidization, and excluding controlling the gas in the chamber accurately.

In addition, the present invention provides a method of manufacturing a feedthrough capable of excluding using added material like the flux or the filler metal in diffusion welding, and excluding metalizing the ceramic.

In addition, the present invention provides a method of manufacturing a feedthrough capable of excluding forming the feedthrough having the nail head, since a shape of the feedthrough is formed by the capillary phenomenon.

In addition, the present invention provides a method of manufacturing a feedthrough capable of removing a gap between the feedthrough and the ceramic hole.

According to an example embodiment, in a method of manufacturing a feedthrough, a ceramic structure is mounted on a mounting groove of a lower jig. The ceramic structure has a plurality of grooves formed uniformly. A platinum/iridium pin formed of platinum and iridium is inserted into the grooves of the ceramic structure. A titanium flange is disposed on the ceramic structure, to form a feedthrough structure having the ceramic structure, the platinum/iridium pin and the titanium flange. The feedthrough structure is disposed on a groove of an upper jig and pressing the feedthrough structure, so that the upper jig is combined with the mounting groove of the lower jig and moves toward a diffusion chamber, for diffusion welding the ceramic structure of the feedthrough structure, the platinum/iridium pin and the titanium flange with each other. A temperature of the diffusion chamber is decreased for cooling the feedthrough structure welded with each other. The ceramic structure of the feedthrough structure is disposed to face a laser machining device. A laser is irradiated to the ceramic structure into which the platinum/iridium pin is inserted, to form a hole in the ceramic structure. A melted platinum/iridium pin moves toward an upper side of the ceramic structure through the hole of the ceramic structure, so that the platinum/iridium pin is partially exposed through the upper side of the ceramic structure In an example, an end portion of the platinum/iridium pin may be in a line with an end portion of the titanium flange.

In an example, the upper jig and the lower jig may include ceramic.

In an example, the ceramic structure may be partially exposed through an outside of the upper jig, when the upper jig is combined with the lower jig.

In an example, the ceramic structure may include a plurality of flow-blocking grooves formed on a surface of the ceramic structure, to block the melted platinum/iridium pin from being flowed on the surface of the ceramic structure.

According to the present example embodiments, more enhanced reproducibility and productivity in the diffusion welding and the laser hole machining may be guaranteed in the present method of manufacturing the feedthrough, compared to the conventional method using the ceramic metallizing and the brazing.

In addition, in the present example embodiment of the method, the flux and the filler metal are unnecessary, and the welding is performed in a state of an oxidized metal so that the strength of the welding is more enhanced. Thus, more enhanced reproducibility and biological adaptation may be guaranteed.

In addition, the metallizing and the coating of nickel (Ni) are unnecessary in the diffusion welding, the total processes are more simplified and the impurities may be prevented from being mixed in the processes.

In addition, the diffusion is performed at an interface between two materials different from each other, and thus the strength of the welding is increased.

In addition, the feedthrough is formed using the laser hole machining, and thus the manufacturing processes are more simplified and the productivity may be more enhanced, compared to the conventional method of casting or forging, in which the casting the platinum/iridium is hard to be performed.

In addition, the feedthrough is formed using the capillary phenomenon and using the laser hole machining, and thus, the gap between the ceramic body and the platinum/iridium pin is decreased. In addition, a spot size of the laser is controlled to form the feedthrough having various kinds of diameters, which means that a number of channels in the predetermined size of feedthrough may be increased.

| * Reference numerals | |
|---|---|
| 1: ceramic structure | 2: platinum/iridium pin |
| 3: titanium flange | 4: lower jig |
| 5, 6: channel | 7: upper jig |
| 8: laser | 9: feedthrough |
| 10, 11: groove | 20: flow-blocking groove |

DETAILED DESCRIPTION

The invention is described more fully hereinafter with Reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Hereinafter, the embodiments of the present invention will be described in detail with reference to the accompanied drawings. In addition, the same reference numerals will be used to refer to the same or like parts and any further repetitive explanation concerning the above elements will be omitted.

Figure 1A:
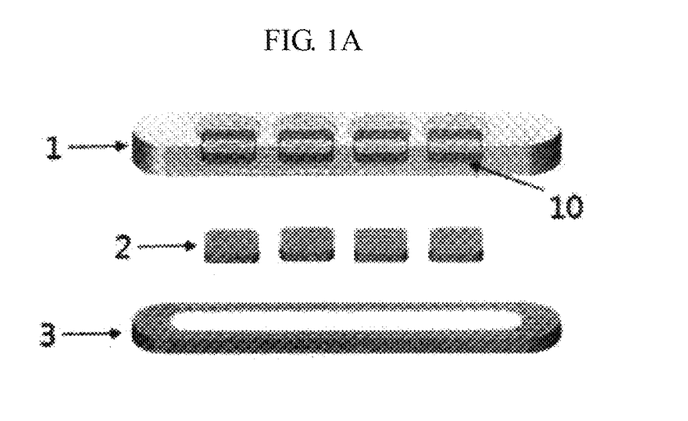
FIGS. 1A to 1C are process views illustrating a method of manufacturing a feedthrough according to the present example embodiment.
Figure 1B:
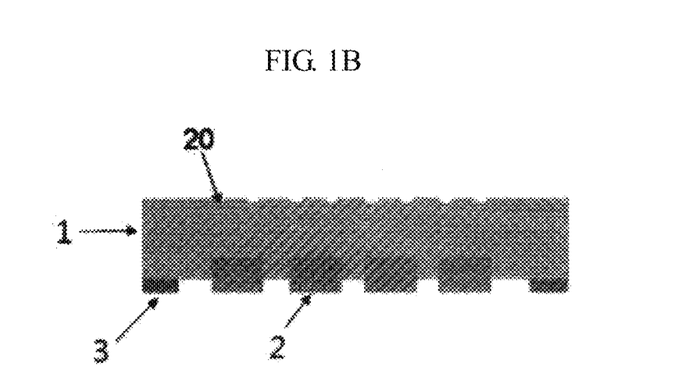
Figure 1C:
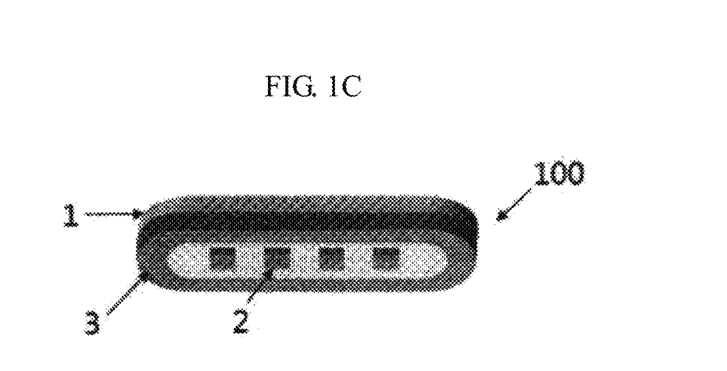

FIGS. 1A to 1C are process views illustrating a method of manufacturing a feedthrough according to the present example embodiment.

Referring to FIGS. 1A to 1C, a feedthrough structure 100 forming a feedthrough 9 includes a ceramic structure 1, a platinum/iridium (90% platinum and 10% iridium) pin 2, and a titanium flange 3.

As illustrated in FIGS. 1A and 1B, a plurality of grooves 10 is uniformly formed on the ceramic structure 1 in which the platinum/iridium pin 2 is positioned. The platinum/iridium pin 2 is in a line with the titanium flange 3 when assembled with each other, for the convenience of manufacturing a jig for diffusion welding.

FIG. 1C illustrates the feedthrough structure 100, the assembly of FIG. 1A. The platinum/iridium pin 2 is disposed inside of the titanium flange 3 having titanium and is partially exposed through the titanium flange 3.

Figure 2:
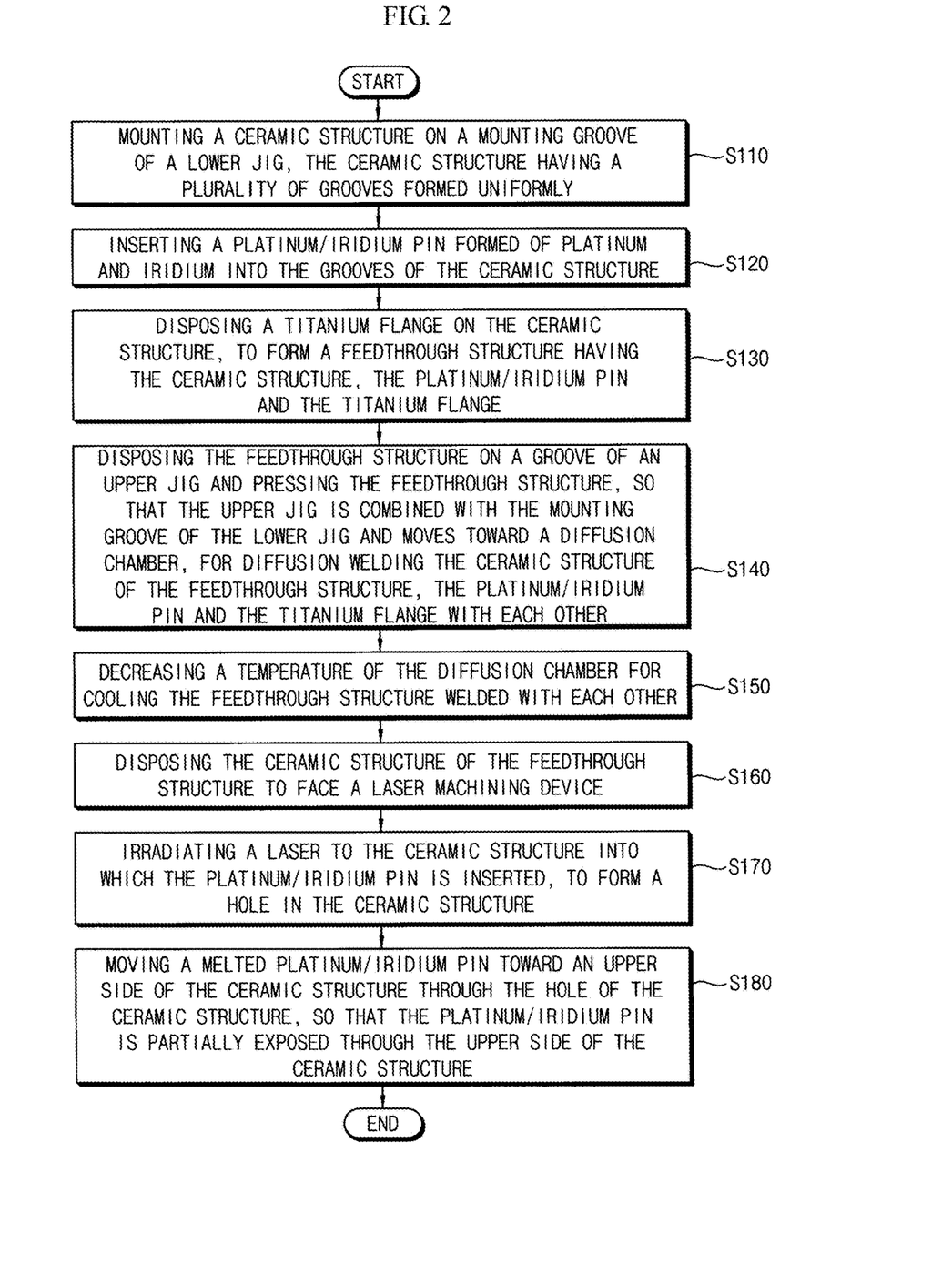
FIG. 2 is a flow chart illustrating the method in FIGS. 1A to 1C.
Figure 3:
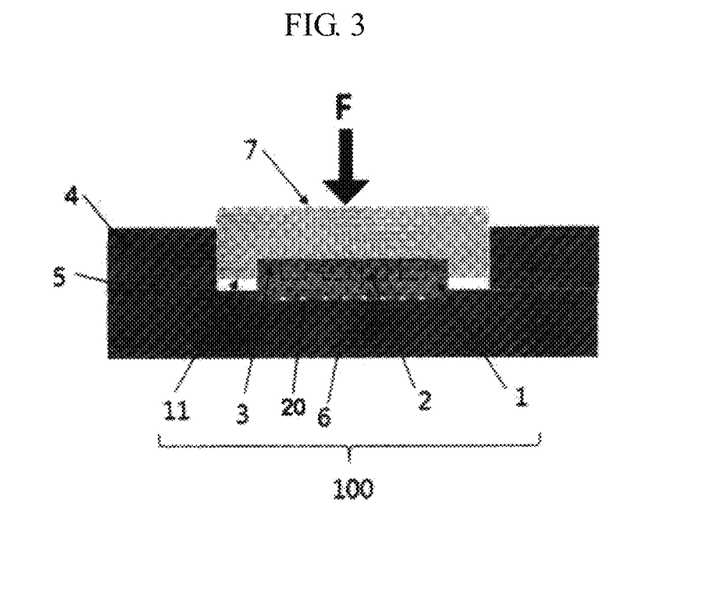
FIG. 3 is a schematic view illustrating the feedthrough combined with upper and lower jigs for diffusion welding.
Figure 4:
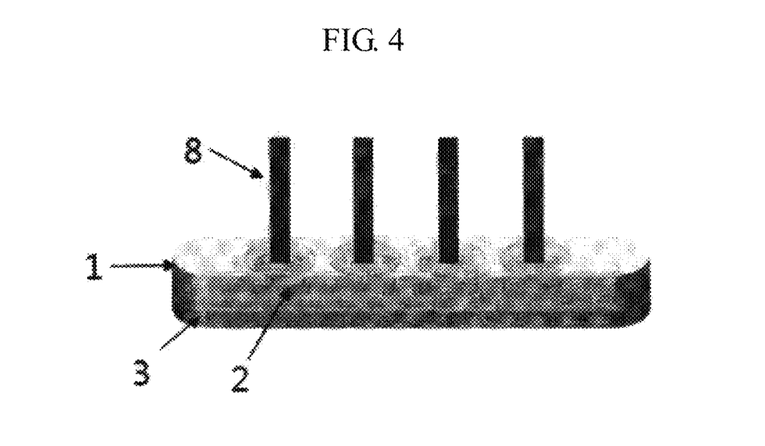
FIG. 4 is a perspective view illustrating a laser hole machining after the diffusing welding of FIG. 3.
Figure 5:
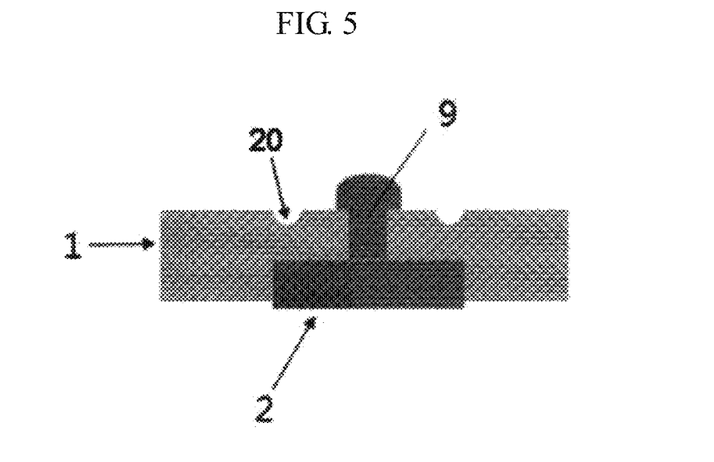
FIG. 5 is a schematic view illustrating forming a pin using capillary phenomenon after the laser hole machining of FIG. 4.

FIG. 2 is a flow chart illustrating the method in FIGS. 1A to 1C. FIG. 3 is a schematic view illustrating the feedthrough combined with upper and lower jigs for diffusion welding. FIG. 4 is a perspective view illustrating a laser hole machining after the diffusing welding of FIG. 3. FIG. 5 is a schematic view illustrating forming a pin using capillary phenomenon after the laser hole machining of FIG. 4.

In a method of manufacturing the feedthrough according to the present example embodiment, as illustrated in FIGS. 1A to 5, first, the ceramic structure 1 is mounted on a mounting groove of a lower jig 4 (Step S110). Here, the ceramic structure 1 has a plurality of grooves 10 formed uniformly.

As illustrated in FIG. 3, the ceramic structure 1 having the grooves 10 uniformly arranged is mounted on the mounting groove of the lower jig 4 (Step S110).

Here, a groove is formed on a bottom surface of the mounting groove of the lower jig 4, so that a portion of the lower part of the ceramic structure 1 may be inserted and combined at the groove on the bottom surface of the mounting groove.

Then, the platinum/iridium pin 2 formed of an alloy of platinum and iridium is inserted into the grooves 10 of the ceramic structure 1 (Step S120).

After combining the platinum/iridium pin 2 with the ceramic structure 1, the titanium flange 3 having titanium is disposed on the ceramic structure 1, to form the feedthrough structure 100 having the ceramic structure 1, the platinum/iridium pin 2 and the titanium flange 3 (Step S130).

Then, the feedthrough structure 100 is disposed on a groove of an upper jig 7. Here, the groove of the upper jig 7 is formed on a lower surface of the upper jig 7. Then, the feedthrough structure 100 is pressed, so that the upper jig 7 is combined with the mounting groove of the lower jig 4 and the upper jig 7 combined with the lower jig 4 moves toward a diffusion chamber. Then, in the diffusion chamber, the ceramic structure 1 of the feedthrough structure 100, the platinum/iridium pin 2 and the titanium flange 3 are welded with each other via a diffusion welding (Step S140). Here, the upper jig 7 is inserted into and is combined with the lower jig 4, to totally separate the feedthrough structure 100 from outer circumstances and to prevent the feedthrough structure 100 from being exposed outside. Thus, the diffusion welding is performed with such sealing circumstances.

Here, two channels 5 and 6 are formed on the lower jig 4, and a gas or an air inside of the space between the lower jig 4 and the upper jig 7 may be exhausted through the channels 5 and 6 when a heat or a pressure is applied during the diffusion welding. The channel 5 is formed at a side surface of the lower jig 4, and the channel 6 is formed at a bottom surface of the lower jig 4.

The upper jig 7 is protruded more compared to an upper surface of the lower jig 4, such that the pressure may be applied with a direction illustrated as an arrow in FIG. 3. Coefficients of thermal expansion of the upper jig 7, the lower jig 4 and the feedthrough structure 100 may be substantially same with each other.

The upper jig 7 is combined with the ceramic structure 1 and then the feedthrough structure 100 moves in a diffusion chamber so that the diffusion welding is performed (Step S140). Then, the feedthrough structure 100 is cooled (Step S150). In the diffusion welding in the diffusion chamber, an atmosphere is less than $10^{-5}$ atm, a pressure over 950 N/m$^2$ is applied, and a heat over than 800° C. is applied during 2 hours. The temperature is increased by 5° C./min and is maintained in a total process of the diffusion welding during 2 hours.

In the cooling, after the diffusion welding, the temperature of the chamber is decreased to cool the welded feedthrough structure 100 (Step S150). For example, in the cooling, the feedthrough structure 100 is cooled in about 17 hours, with a velocity of 1° C./min. In addition, in the cooling, the feedthrough structure 100 should not be exposed to a cool gas or cool circumstances, and the heater is gradually cooling down with the velocity of 1° C./min.

Then, the cooled ceramic structure 1 of the feedthrough structure 100 is positioned to face a laser machining device as illustrated in FIG. 4 (Step S160), a laser is irradiated to the ceramic structure 10 into which the platinum/iridium pin 2 is inserted, and then the hole is formed through the ceramic structure 1 (Step S170).

Then, a melted platinum/iridium pin 2 moves toward an upper surface of the ceramic structure 1 through the hole of the ceramic structure 1, so that the platinum/iridium pine 2 is partially exposed through the upper side of the ceramic structure 1 (Step S180). An end portion 9 of the platinum/iridium pin 2 exposed through the ceramic structure 1 is to be the feedthrough 9 electrically connected to an electric stimulating circuit or an external stimulating electrode.

The ceramic structure 1 may further include a plurality of flow-blocking grooves 20 formed on the surface of the ceramic structure 1, so that the melted platinum/iridium pin 2 is prevented from being flowed on the surface of the ceramic structure 1.

The flow-blocking grooves 20 are formed on the surface of the ceramic structure 1 having the grooves 10 into which the platinum/iridium pin 2 is inserted. When the platinum/iridium pin 2 is melted on the grooves 10 in which the platinum/iridium pin 2 is inserted, the melted platinum/iridium pin 2 is prevented from being flowed on the surface of the ceramic structure 1.

The melted platinum/iridium pin 2 is flowed in the flow-blocking grooves 20, and thus the flow-blocking grooves 20 prevent the melted platinum/iridium pin 2 from being flowed on the surface of the ceramic structure 1.

Here, the flow-blocking grooves 20 are formed on the surface of the ceramic structure 1 opposite to the surface on which the grooves 10 are formed.

Thus, the melted platinum/iridium pin 2 of one of the grooves 10 is flowed in the flow-blocking grooves 20 adjacent to the grooves 10, and thus the melted platinum/iridium pin 2 of the groove 10 is prevented from being flowed into the adjacent groove 10. Thus, the melted platinum/iridium pin 2 from the groove 10 is prevented from facing the melted platinum/iridium pin 2 from the adjacent groove 10.

Accordingly, the melted platinum/iridium pins 2 adjacent to each other are prevented from being mixed with each other and from being connected to each other.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A method of manufacturing a feedthrough comprising:
   mounting a ceramic structure on a mounting groove of a lower jig, the ceramic structure having a plurality of grooves formed uniformly;
   inserting a platinum/iridium pin formed of platinum and iridium into the grooves of the ceramic structure;
   disposing a titanium flange on the ceramic structure, to form a feedthrough structure having the ceramic structure, the platinum/iridium pin and the titanium flange;
   disposing the feedthrough structure on a groove of an upper jig and pressing the feedthrough structure, so that the upper jig is combined with the mounting groove of the lower jig and moves toward a diffusion chamber, for diffusion welding the ceramic structure of the feedthrough structure, the platinum/iridium pin and the titanium flange with each other;
   decreasing a temperature of the diffusion chamber for cooling the feedthrough structure welded with each other;
   disposing the ceramic structure of the feedthrough structure to face a laser machining device;
   irradiating a laser to the ceramic structure into which the platinum/iridium pin is inserted, to form a hole in the ceramic structure; and
   moving a melted platinum/iridium pin toward an upper side of the ceramic structure through the hole of the ceramic structure, so that the platinum/iridium pin is partially exposed through the upper side of the ceramic structure.

2. The method of claim 1, wherein an end portion of the platinum/iridium pin is in a line with an end portion of the titanium flange.

3. The method of claim 1, wherein the upper jig and the lower jig include ceramic.

4. The method of claim 1, wherein the ceramic structure is partially exposed through an outside of the upper jig, when the upper jig is combined with the lower jig.

5. The method of claim 1, wherein the ceramic structure includes a plurality of flow-blocking grooves formed on a surface of the ceramic structure, to block the melted platinum/iridium pin from being flowed on the surface of the ceramic structure.

* * * * *